United States Patent [19]

Kerr et al.

[11] 4,210,746

[45] Jul. 1, 1980

[54] NUCLEOTIDE INHIBITOR OF PROTEIN SYNTHESIS

[75] Inventors: Ian M. Kerr, London; Ronald E. Brown, Hemel Hempstead; Ara G. Hovanessian, London, all of England

[73] Assignee: National Research Development Corporation, England

[21] Appl. No.: 932,488

[22] Filed: Aug. 10, 1978

[51] Int. Cl.$^2$ .................. C07H 17/00; C07H 15/12
[52] U.S. Cl. ........................ 536/27; 536/28; 536/29
[58] Field of Search ............ 536/27, 28, 29; 424/19, 424/38

[56] References Cited

U.S. PATENT DOCUMENTS 3,534,017  10/1970  Fuzimoto et al. .................. 536/29

OTHER PUBLICATIONS

Sawai, H., J. Am. Chem. Soc., vol. 98 (1976), 7037–7039.
Sawai, H., et al., J. Am. Chem. Soc., vol. 97 (1975), 3532–3533.

*Primary Examiner*—Johnnie R. Brown
*Assistant Examiner*—Blondel Hazel
*Attorney, Agent, or Firm*—Jacobs & Jacobs

[57] ABSTRACT

Compounds having properties as inhibitors of protein synthesis are disclosed, of the general formula

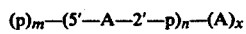

$$(p)_m\text{—}(5'\text{—}A\text{—}2'\text{—}p)_n\text{—}(A)_x$$

wherein
  p represents the phosphate group (orthophosphate),
  m is 0, 2, or 3
  A represents adenosine,
  n is from 2 to 5,
  x is 0 or 1, said compound containing at least three adenosine residues, the figures 5' and 2' signifying the carbon atoms of the ribose ring to which the respective phosphate groups p are attached.

Compounds of particular interest are ApApA and its phosphorylated derivatives ppApApA and pppApApA. The substances may be prepared by chemical synthesis or enzymatic synthesis. They may be incorporated in liposomes.

5 Claims, No Drawings

NUCLEOTIDE INHIBITOR OF PROTEIN SYNTHESIS

This invention relates to protein synthesis in living cells and more particularly to inhibition of the synthesis of viral protein.

One of the most important developments in the field of virology in recent times has been the discovery of interferon by Isaacs and Lindenmann in 1957. Since that time the role of interferon in inhibiting the growth of viruses in the laboratory and in clinical situations has been the subject of extensive investigation by many workers and as a consequence there has been a significant advance in knowledge of virus replication and behaviour in living cells and an indication of the clinical applications of interferon in certain types of viral infection. It has long been recognised that interferon does not act directly on viruses but is mediated through other substances.

In our previous studies on protein synthesis in systems derived from interferon treated cells, described in Nature, 264 1976 pages 477–480, we have suggested that certain observed inhibitory effects may be due to interferon-mediated substances, notably a protein kinase and a low molecular weight inhibitor. Our subsequent research on the nature of the latter substance has also enabled us to disclose that it appears to be an oligonucleotide.

We have now found how the inhibitor can be prepared enzymatically, isolated, and structurally characterised and this has led in turn to the preparation of inhibitory compounds by chemical synthesis.

The present invention comprises compounds having the general formula (p)$_m$—(5'—A—2'—p)$_n$—(A)$_x$ wherein
p represents the phosphate group (orthophosphate),
m is 0, 2, or 3,
A represents adenosine,
n is from 2 to 5
x is 0 or 1,
said compound containing at least three adenosine residues, the figures 5' and 2' signifying the carbon atoms of the ribose ring to which the respective phosphate groups p are attached.

It will be appreciated that the simplest compound corresponding to the above structure is one which, by omitting reference to the 5', 2' carbon connections which are hereafter assumed as implied, may be designated ApApA. Of slightly greater complexity are the phosphorylated derivatives of this such as, for example the diphosphate ppApApA and the triphosphate pppApApA. The structure of the latter compound is illustrated on the next page, where B represents adenine from which the repeating Ap unit and its 5' and 2' carbon atom linkages are clearly apparent.

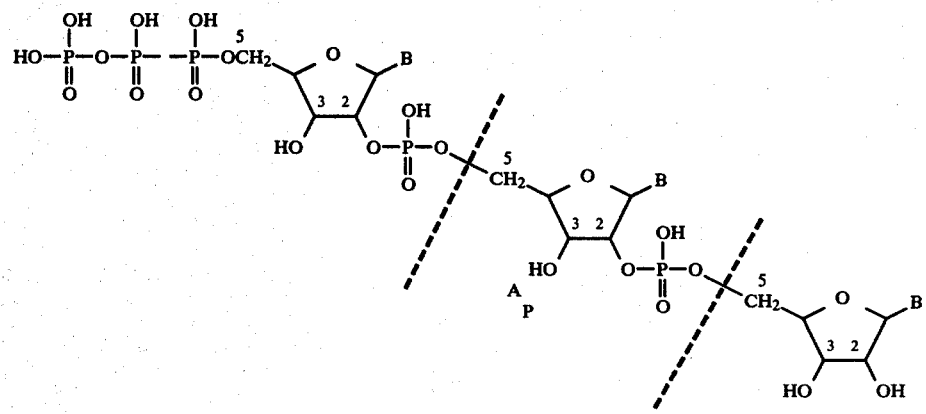

the 5', 2' structure indicated above is rare in nucleotide chemistry, and has not previously been demonstrated in biologically prepared substances, where the corresponding 5', 3' structure is more usual. Methods for preparing some 5', 2' linked substances have been described although the biological properties associated with the 5', 2' structure have not been appreciated hitherto. For example 5', 2'-linked pApApA and pApApApA are known from J.A.C.S. 97, 1975 3532.

Compounds in which m is zero are a convenient group of precursors of more active substances and such compounds are more easily taken up by cells. The expression of their activity in the cell, however, is enhanced by phosphorylation by enzymes naturally present in the cell. Introduction of 5'-phosphorylated compounds into cells is facilitated by incorporation in liposomes.

To prepare compounds in accordance with the invention, general methods are available in the literature and notably those described by A. M. Michelson in "The Chemistry of the Nucleosides and Nucleotides", Academic Press 1963 e.g. at Pages 418, 419 and elsewhere and also by the same writer in J. Chemical Society 1959, 1371–1395 and 3655–3669. These methods are described mainly in relation to the preparation of the more conventional 5', 3' linked structures but may be readily applied to the purposes of the present invention.

Thus, treatment of certain quaternary ammonium salts of the starting material, usually a mixed (2' or 3') monophosphate, with tetraphenyl pyrophosphate or diphenyl phosphorochloridate and tri-n-butylamine in anhydrous dioxan readily produces a cyclic phosphate in which the 2' and 3' hydroxyl groups are bridged by a phosphate group. Further addition of the reagents causes polymerisation of the cyclic phosphate, giving rise to a mixture of oligonucleotides in which the trimer is usually a main component. Mild acid hydrolysis of the reaction mixture opens the terminal cyclic phosphate to give oligonucleotides with a terminal 2'- or 3'-phosphate group.

It will be appreciated that the two possible linkages at which the cyclic phosphate will break to combine with the terminal CH$_2$OH group of the reacting co-monomer will give rise to the 5'2' and 5'3' isomers of the final products, probably in approximately equal proportions. The mixed products obtained in this way may be separated by selective destruction of 5'3' linked compounds with enzymes e.g. T2-ribonclease. The resulting mixture is separated e.g. by chromatography to recover the desired oligomer or oligomers from which the terminal 3'-phosphate group is removed enzymatically e.g. with bacterial alkaline phosphatase. At this stage the product has the structure ApApA or higher oligomers of repeating units of Ap in which the linkages are 2'-5'.

Conversion of the ApApA type structure into 5'-phosphorylated derivative e.g. pApApA, ppApApA, and pppApApA may be effected in stages. The first stage may be conveniently achieved by enzymatic introduction of a 5'-monophosphate group and subsequent stages may be carried out chemically by known methods.

An alternative chemical method of preparing compounds of this invention, especially the 5'-phosphorylated 2'5' linked oligoadenylic acids, is by application of the chemical method described in J.A.C.S. 97 (1975) 3532 and 98 (1976) 7037-7039. The method involves condensation in aqueous solution of adenosine 5'phosphorimidazolide in the presence of divalent metal ions.

Compounds where x is 0 can be derived from compounds where x is 1 by periodate oxidation and β-elimination of the terminal A residue according to known methods.

A further method of preparing the compounds of this invention is by enzymatic synthesis. It has been found that rabbit reticulocytes contain a synthetase which can cause adenosine triphosphate to polymerise in 2'5' linked units and therefore a lysate of such cells can be used for the purpose of the invention.

The invention is further described in the following Examples.

EXAMPLE 1

1. 9.0 g Adenosine 2'(3') monophosphate(Sigma, free acid) and 11.4 g tri-n-decylamine are added to 300 ml methanol/ethanol (1:1). The insoluble is refluxed for 90 min. A small amount (<50 mg) of insoluble material that remains is filtered (sintered glass filter) and the filtrate rotary evaporated to dryness. Benzene (dried over sodium, 100 ml) is added and and the rotary evaporation repeated. The addition and evaporation of benzene is repeated to dry the solid to constant weight in vacuo (<1 mm Hg) over P$_2$O$_5$. Yield 19.2 g of the tri-n-decylamine salt of AMP.

10 g of the tri-n-decylamine salt of 2'(3') AMP is dissolved in 100 ml AR dioxan and 3.85 ml diphenylphosphorochloridate added over 2 min (magnetic stirring). The solution goes cloudy. Then 8.85 ml tri-n-butylamine is added over 2 min and the clear solution is stirred for 2 hours. All manipulations are at room temperature (~20°). A further 3.85 ml diphenylphosphorochloridate and 8.85 ml tributylamine are then added, causing the solution to become cloudy and form a slight precipitate. After a further 4 h., 5 volumes of petroleum ether 40/60 are added with stirring. The supernatant is decanted and the insoluble residue treated with 3×400 mls ether with stirring. Each time the supernatant is decanted from the white solid. The solid is finally dried in vacuo to give 8.3 g of a pale yellow solid (Ap)$_n$A>p.

8.3 g (Ap)$_n$A>p is treated with 350 ml 0.1 N HCl for 4 hours (magnetic stirring). Part of the material is insoluble. The supernatant is decanted, neutralised to pH 7.3 with NH$_4$OH and lyophilised.

2. Removal of 3'-5' linked oligoadenylic acids by digestion with T2-ribonuclease 3gm of crude oligoadenylic acid (containing variable amounts of NH$_4$Cl and about 20% oligoadenylic acid) is dissolved in 40 ml water and the pH adjusted to 4.5 with 1 N acetic acid. Add 100 units of T2-ribonuclease (Sigma Chemical Co.) for each 10,000 O.D.$_{260}$ units of oligoadenylic acid and incubate overnight at 37° C. (1 O.D.$_{260}$ unit=1 ml of a solution giving an absorbance of 1 in a 1 cm pathlength cell at 260 nm and is equivalent to approximately 22 g of oligoadenylic acid). Add a further 50 units of T2-ribonuclease per 10,000 O.D.$_{260}$ units of oligoadenylic acid and continue the incubation a further 6-8 hr. Adjust the pH to 7.8 with ammonium hydroxide and dilute to 100 ml with water. Warm (40°-50° C.) briefly to dissolve any insoluble material. Centrifuge at 2500× g for 10 min and discard pellet.

3. Chromatographic purification of 2'-5' linked ApApAp

Dilute the supernatant from the previous step with an equal volume (100 ml) of 0.2 M NH$_4$HCO$_3$ and load onto a column (2.5 cm×70 cm) of DEAE Sephadex A25 (Pharmacia) equilibrated with 0.2 M NH$_4$HCO$_3$. Wash the column with 200 ml of 0.2 M NH$_4$HCO$_3$ and elute with 0.5 M NH$_4$HCO$_3$. The 2'-5' ApApAp elutes between 1200 and 1300 ml of 0.5 M NH$_4$HCO$_3$ and is detected by reading the O.D.$_{260}$ of the eluate. In a typical separation A2'p5A2p5Ap accounts for about 10% (2,000 O.D.$_{260}$ units) of the initial mixture (20,000 O.D.$_{260}$ units).

4. Removal of the 3'-phosphate with bacterial alkaline phosphatase

The A2'p5'A2'p5'Ap is lyophilised, taken up in water to a concentration of 100 O.D.$_{260}$ units/ml and adjusted to pH 7.5 with 1 M ammonium hydroxide or acetic acid. Digest for 18 hr at 37° C. with 2 units of bacterial alkaline phosphatase (BAP, Sigma Chemical Co.) per 100 O.D.$_{260}$ units.

After lyophilisation the BAP is removed by chromatography on a column (1.5 cm×30 cm) of Sephadex G.25 (fine; Pharmacia) equilibrated and eluted with water. At least 80% (1600 O.D.$_{260}$ units) of the starting material should be recovered as a single peak of A2'p5'A2'p5'A.

5. Enzymic addition of the 5'-phosphate and isolation of pA2'p5'A2'p5'A

A2'p5'A2'p5'A (100 O.D.$_{260}$ units/ml) is incubated at 37° C. with poly-nucleotide kinase (200 units/ml, PL Biochemicals Ltd.) in 80 mM Tris HCl pH 7.6, 10 mM magnesium acetate 24 mM ATP and 14 mM 2-mercaptoethanol until there is no further conversion to pApApA (usually 30 to 40%). The incubation mixture is heated to 90° C. for 5 min to destroy the polynucleotide kinase, diluted with an equal volume of 0.2 M NH$_4$HCO$_3$ and loaded onto a column (1.5 cm×50 cm) of DEAE Sephadex A.25 (Pharmacia) equilibrated in 0.2 M NH$_4$HCO$_3$. The pA2p5A2p5A elutes last and comes off during the final elution with 0.6 M salt.

6. Chemical synthesis of pppA2' p5'A2'p5'A and ppA2'p5' A2'P5'A from pA2'p5'A2'p5'A The method used is based on that of Smith and Khorana (Journal of the American Chemical Society 80, (1958) 1141).

The yield of pA2'p5'A2'p5'A (60 O.D.$_{260}$ units, approx 1.3 mg) from a 200 µl reaction of the above type was lyophilised and taken up in 100 µl of 20% tri-n-butylamine in pyridine. 15 µl of phosphoric acid and 200 mg of dicyclohexylcarbodiimide were added, the mixture stirred at room temperature for 40 hr, diluted with water (3 ml), filtered and the precipitate washed with water (3 ml×3). The combined filtrates were extracted with ether (5×10ml) lyophilised, taken up in 2.5 ml water, the pH adjusted to 7 with 1 M NH$_4$OH and loaded onto a column of DEAE cellulose (Whatman DE32 microgranular) equilibrated with 10 mM KCl, 1.5 mM magnesium acetate, 20 mM Hepes buffer pH 7.5. The column was washed with the same buffer, with 100 mM KCl, 1.5 mM magnesium acetate, 20 mM Hepes pH 7.5 and the product eluted with 350 mM KCl, 1.5 mM magnesium acetate, 20 mM Hepes pH 7.5. In the example given the yield of biologically active pppA2'p-5'A2'p5'A and ppA2'p5'A2'p5'A was 1.5 O.D.$_{260}$ units (approximately 40 µg).

7. To produce the higher oligomers the procedure of (3) is continued and elution is continued in the same buffer to yield sequentially (Ap)$_4$, (Ap)$_5$, (Ap)$_6$ etc. These are then submitted to subsequent treatment as described in sections (4) onwards.

8. ppA2'p5'A2'p5'A (7 mM) was entrapped in positively charged unilamellar liposomes (phosphatidyl choline:steroylamine: cholesterol, 8:2:6). Exposure of monolayer cultures of BHK cells to such liposomes resulted in a 50% inhibition of protein synthesis over a period of one hour.

ENZYMATIC SYNTHESIS OF pppA2'p5'A2'p5'A AND RELATED BIOLOGICALLY ACTIVE COMPOUNDS

EXAMPLE 2

A column (30 ml) of poly(C) Sepharose (PL Biochemicals) was washed with 1 liter of 90 mM KCl, 1.5 mM magnesium acetate, 7 mM 2-mercaptoethanol, 20 mM Hepes buffer pH 7.5 containing 20% v:v glycerol (DBG). 65 ml of rabbit reticulocyte lysate containing a 2'5'-A-synthetase was applied slowly to the column over 1 hr at room temperature and the column washed with 1 liter of DBG.

The enzyme bound to the poly(I).poly(C) Sepharose, was resuspended in 180 ml of 50 mM KCl, 8 mM magnesium acetate, 7 mM 2-mercaptoethanol, 20 mM Hepes pH 7.5 and 3 mM adenosine triphosphate (ATP) containing 20% v:v glycerol and incubated with gentle shaking at 30° C. for 4 days. The incubation medium was replaced each day with a fresh batch. The supernatants (4×175 ml) were combined, 6 volumes of acetone were added, the mixture held overnight at −20° C. and centrifuged at 2,500× g for 10 min at 4° C. The pellets were taken up in 75 ml of 10 mM KCl, 1.5 mM magnesium acetate, 20 mM Hepes pH 7.5, centrifuged as above and the supernatant loaded onto a column (1.5 cm×27 cm) of DEAE cellulose (Whatman DE32 microgranular) equilibrated in the same buffer. The column was washed with 1 liter of the same buffer and then with 450 ml of 100 mM KCl, 1.5 mM magnesium acetate, 20 mM Hepes pH 7.5 to remove residual ATP and related bi-products. The desired product was eluted with 150 ml of 350 mM KCl, 1.5 mM magnesium acetate, 20 mM Hepes pH 7.5, diluted therefore with water, precipitated with 6 volumes of acetone and recovered by centrifugation as above. The pellet was taken up in 5.0 ml of water adjusted to pH 7 with M NH$_4$OH. The yield was 1100 O.D.$_{260}$ units or approximately 29 mg. The major component (40 to 90%) in this biologically active product was pppA2'p5'A2'p5'A the other components being the corresponding dimer (pppA2'p5'A), tetramer [ppp(A2'p)$_3$A], pentamer [ppp(A2'p)$_4$A] and higher oligomers in decreasing amounts. The trimer, tetramer and pentamer have similar biological activity. The dimer is at least ten thousand fold less potent than these. All preparations contain small amounts (5 to 30%) of the corresponding oligomer diphosphates which have similar biological activity to the triphosphates.

A2'p5'A2'p5'A (or other oligomers) can be obtained from pppA2'p5'A2'p5'A (or corresponding oligomers) by digestion with bacterial alkaline phosphatase and the A2'p5'A2'p5'A isolated on Sephadex G25 as described in Example 1.

The compounds of this invention are highly potent inhibitors of protein synthesis. For example pppApApA is active in the inhibition of protein synthesis at subnanomolar levels in cell free systems from mouse L-cells or rabbit reticulocytes. It has been tested for activity in whole cells with and without removal of the terminal triphosphate by prior treatment with bacterial alkaline phosphatase and its effect on both host and viral RNA synthesis examined. The inhibitor shows at 50 percent reduction of RNA synthesis. The combination of the inhibitor and virus infection appears more cytotoxic than either agent alone, suggesting that the inhibitor treated cell may suicide on virus infection thus preventing or reducing virus growth and the spread of infection. Pronounced inhibition has also been demonstrated in BHK cells using ApApA or pppApApA the latter being delivered to the cells in liposome formulations. In view of their interferon-like properties and relationship to the interferon phenomenon the compounds are also of interest in relation to tumour growth, in which connection the properties of interferon are well established.

We claim:

1. A compound of the formula

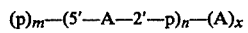

wherein
 p is orthophosphate,
 m is 0, 2, or 3
 A is adenosine,
 n is from 2 to 5 and
 x is 0 or 1,
said compound containing at least three adenosine residues, the figures 5' and 2' signifying the carbon atoms of the ribose ring to which the respective phosphate groups p are attached.

2. A compound according to claim 1 having the structure ApApA.

3. A compound according to claim 1 having the structure ppApApA.

4. A compound according to claim 1 having the structure pppApApA.

5. A preparation comprising a compound according to claim 1 incorporated into liposomes.

* * * * *